(12) United States Patent
Spearman et al.

(10) Patent No.: US 10,265,201 B2
(45) Date of Patent: Apr. 23, 2019

(54) DEGRADEABLE OSTIAL STENT

(71) Applicants: Michael R. Spearman, The Woodlands, TX (US); John Henry Burban, Lake Elmo, MN (US); John William Shanahan, White Bear Lake, MN (US); Keith A. Roberts, Dellwood, MN (US); Peter Joseph Catalano, Newton, MA (US)

(72) Inventors: Michael R. Spearman, The Woodlands, TX (US); John Henry Burban, Lake Elmo, MN (US); John William Shanahan, White Bear Lake, MN (US); Keith A. Roberts, Dellwood, MN (US); Peter Joseph Catalano, Newton, MA (US)

( * ) Notice: Subject to any disclaimer, the term of this patent is extended or adjusted under 35 U.S.C. 154(b) by 65 days.

(21) Appl. No.: 15/266,659

(22) Filed: Sep. 15, 2016

(65) Prior Publication Data
US 2018/0071118 A1 Mar. 15, 2018

(51) Int. Cl.
*A61F 2/82* (2013.01)
*A61L 31/14* (2006.01)

(52) U.S. Cl.
CPC .............. *A61F 2/82* (2013.01); *A61L 31/148* (2013.01); *A61F 2210/0004* (2013.01); *A61F 2210/0061* (2013.01); *A61F 2210/0076* (2013.01); *A61F 2230/001* (2013.01); *A61F 2230/0069* (2013.01); *A61F 2250/003* (2013.01); *A61F 2250/0036* (2013.01); *A61F 2250/0056* (2013.01); *A61L 2300/604* (2013.01); *A61L 2300/608* (2013.01); *A61L 2420/08* (2013.01)

(58) Field of Classification Search
CPC ................ A61F 2/82; A61F 2210/0004; A61F 2210/0061
See application file for complete search history.

(56) References Cited

PUBLICATIONS

Barros et al., Bioresorbable uteral stents from natural origin polymers, 2014, J Biomed Mater Res Part B, Wiley Periodicals, pp. 1-10.*

* cited by examiner

*Primary Examiner* — Brian A Dukert
(74) *Attorney, Agent, or Firm* — Mark A. Litman & Assoc. P.A.

(57) ABSTRACT

A polymeric stent having a length, an outer surface and a cross-section. A lumen passes through the entire length, the lumen having a surface forming an equivalent diameter in the polymeric stent. The polymeric stent includes a first aqueous-swellable, biocompatible and biodegradable composition (e.g., polymer) having a thickness. The aqueous-swellable and biodegradable polymer retaining structural integrity for at least 1 hours up to thirty days when swollen and kept moist by a moist aqueous environment. Barrier layers of biodegradable polymer(s) may be used to prevent migration of liquids into the lumen.

10 Claims, 4 Drawing Sheets

DEGRADEABLE OSTIAL STENT

BACKGROUND OF THE INVENTION

Field of the Invention

The present invention relates to the field of medical treatments in body cavities or passages, and particularly non-arterial stent placement, and especially ostial stent placement.

BACKGROUND OF THE ART

There are a significant number of medical conditions and their attendant treatments that require maintaining fluid flow and/or continuity within specific regions of the human anatomy. The most common method of fluid flow maintenance is through the use of stents. Stents have been used in many different positions, including vascular (arterial and venal) stents, organ duct stents, lachrymal stents, ear drum tubes, ostial stents and the like. Although each type of stent is a variant in structure and composition of a tube-like element, the dimensions, compositions, and properties of the stents must differ from each environment to properly function. For example, the metal, composition or polymeric stents used in vascular stenting (where a more permanent implantation is desired) would be inappropriate for ear drum stenting or lachrymal stents, which tend to be more temporary insertions.

Many different structures and compositions are known in this field of technology, and some of them are described in the prior art noted below.

US Patent Publication No. 20160024285 (Delli-Santi) describes a resilient foam and methods of making the foam. The resilient foam includes a derivatized polyanionic polysaccharide and has an open-cell structure. When the resilient foam is contacted with water, the foam forms a thixotropic hydrogel. A wide range of polyanionic polysaccharides are suitable for the invention Non-limiting examples of polyanionic polysaccharides include starch and cellulose. Non-limiting examples of derivatized polyanionic polysaccharides include carboxymethyl cellulose, cellulose ethyl sulfonate, carboxymethyl amylose, chondroitin-6-sulfate, chondroitin-4-sulfate, dermatan sulfate, alginate, heparin, heparin sulfate, or any combination thereof. In some embodiments, the derivatized polyanionic polysaccharide is dissolvable. The resilient foam can include 40 wt. % or more of derivatized polyanionic polysaccharide.

Bioresorbable gels and stents are also described in U.S. Pat. No. 8,313,762, and U.S. Patent Application Publication No. 2003/0187381.

US Patent Publication 20150306282 (Scanlon) describes a high strength, bioresorbable wall thickness suitable for use in an endoprosthesis such as a stent that is produced by first forming a wall thickness by melt processing or solution processing one or more bioresorbable materials into a tubular shape; drawing the shape from shorter length to an optimum longer length and reducing the diameter from a larger diameter to a smaller diameter to orient the molecular chains of the material; fabricating a stent from the tube formed of the oriented material by cutting a strut pattern in its wall thickness; covering the stent's struts with at least one coating to delay degradation of the bioresorbable material; covering the stent's struts with one or more controlled release active ingredients to minimize the risk of restenosis or other side effects; crimping the stent onto a balloon catheter assembly; delivering the stent into an anatomical lumen via percutaneous methods to a treatment location; radially expanding the stent from a smaller size to a larger size at the treatment location wherein the stent temporarily supports the anatomical lumen; and removing the catheter from the lumen. Many categories of stents, including nasal stents are disclosed.

U.S. Pat. No. 8,974,486 (Kotler) provides methods and devices for maintaining nasal passages open after nasal surgery. The post-operative device includes a first tubular member with a first proximal end and a first distal end, and a second tubular member with a second proximal end and a second distal end, where the first proximal end is connected to the second proximal end with a bridging member. The method includes inserting the post-operative device into the nasal passages and before, during or after inserting the device into the nasal passages, adjusting the medical device to accommodate the nasal passages by manipulating a flexible member of the medical device.

The endoprosthesis of that invention includes applications selected from the group of: coronary vascular stent; a vascular stent; a peripheral vascular stent; a carotid stent; a cerebral stent; a cell transportation device; a cell growth platform; a device for supporting an anatomical lumen; a device for reinforcing an anatomical lumen; a device for delivering a drug or drugs to an anatomical lumen; a renal stent; a iliac stent; a superficial femoral artery stent; a urethral stent; a ureter stent; a urinary stent; a biliary stent; an implantable scaffold; a tracheal stent; a trachea stent; a large bronchi stent; a nasal stent; a gastrointestinal stent; an esophageal stent; a drug delivery stent; a drug delivery device; a self-expandable stent; a balloon-expandable stent; a coil stent; a helical spiral stent; a woven stent; an individual ring stent; a ratcheting stent; a modular stent; a bifurcated stent; a stent-graft; a graft; a birth control device; an intrauterine device (IUD); an anatomical lumen repair or splicing device; a device for local delivery of active ingredients to tubular shaped lumen or organs for treatment of cancer; a device for treatment of colon or rectal cancer; an implant; a patch; a mechanical support device; a reinforcement device; a repair device; an attachment device; an oncology treatment device; a device for treatment of cancer within or near an anatomical lumen; a device to assist in remodeling of diseased anatomical lumens; a tissue engineering application (bone, cartilage, blood vessels, bladder, skin, muscle, etc.); a bone fixation device; bone plates; a medical textile; a repair, a device for reconstruction, or replacement/repair of ligaments; a device for maxillofacial surgery; a device for repair, reconstruction, or replacement of rotator cuffs; a device for repair, reconstruction, replacement of hollow organ tissue; a screw; a plate; any implantable devices, patches, regenerative medicine; and a device for the treatment of cancer An ENT stent may be a choanal atresia stent composed of two long hollow tubes that are bridged by a flexible transverse tube. See, e.g., U.S. Pat. No. 6,606,995. The ENT stent may be an expandable nasal stent for postoperative nasal packing composed of a highly porous, pliable and absorbent foam material capable of expanding outwardly, which has a non-adherent surface. See, e.g., U.S. Pat. No. 5,336,163. The ENT stent may be a nasal stent composed of a deformable cylinder with a breathing passageway that has a smooth outer non-absorbent surface used for packing the nasal cavity following surgery. See, e.g., U.S. Pat. No. 5,601,594. The ENT stent may be a ventilation tube composed of a flexible, plastic, tubular vent with a rectangular flexible flange which is used for the nasal sinuses following endoscopic antrostomy. See, e.g., U.S. Pat. No. 5,246,455. The ENT stent may be a ventilating ear tube composed of a shaft and an extended tab which is used for equalizing the pressure between the middle ear and outer ear. See, e.g., U.S. Pat. No. 6,042,574. The ENT stent may be a middle ear vent tube composed of a non-compressible, tubular base and an eccentric flange. See, e.g., U.S. Pat. No. 5,047,053. ENT stents, which may be combined with the compounds according to the present disclosure, include commercially available products such as Genzyme Corporation (Ridgefield, N.J.) SEPRAGEL Sinus Stents, the MEROGEL Nasal Dressing and Sinus Stents from Medtronic Xomed Surgical Products, Inc. (Jacksonville, Fla.), the POLYFLEX Stent from Rusch (Germany), and the FREEMAN Frontal Sinus Stent from InHealth Technologies (Carpinteria, Calif.). Other exemplary products which may be combined with the compounds described include the RELIEVA Balloon Sinuplasty (Acclarent Inc., Menlo Park, Calif.) catheter-based devices made of flexible tubes with a balloon on the distal end. These devices are configured to track over the sinus guidewire to the blocked ostium, which is then gradually inflated to gently restructure the ostium and are intended for clearing blocked sinuses, restoring normal sinus drainage and function, and preserving normal anatomy and mucosal tissue. See, for example, US Patent Applications 2006/0210605; 2006/0063973; and 2006/0095066.

US Patent Publication No. 20050191331 (Hunter) describes implants that are used in combination with an anti-scarring agent in order to inhibit scarring that may otherwise occur when the implant is placed within an animal. The agent may be any suitable anti-scarring agent, e.g., a cell cycle inhibitor, and may be used in conjunction with a second pharmaceutical agent, e.g., an antibiotic. Suitable implants include intravascular implants, a vascular graft or wrap implant, an implant for hemodialysis access, an implant that provides an anastomotic connection, ventricular assist implant, a prosthetic heart valve implant, an inferior vena cava filter implant, a peritoneal dialysis catheter implant, a central nervous system shunt, an intraocular lens, an implant for glaucoma drainage, a penile implant, a endotracheal tube, a tracheostomy tube, a gastrointestinal device, and a includes spinal implant.

All cited documents are incorporated herein by reference in their entirety.

Stents, and especially ostial stents having properties determined to be specific to that environment are desirable. The present technology enables low cost, fast self-securing, efficient ostial stents that resorb in the body under normal conditions, and thus mitigate the potential for adverse reactions derived from the location of a foreign body in the sinus cavities.

SUMMARY OF THE INVENTION

A polymeric stent comprising a polymeric body having a length, an outer surface and a cross-section. The body may be a continuous dense polymeric matrix or may be a foam structure. A lumen passes through the entire length, the lumen having a surface that is an internal equivalent diameter of the polymeric body. The polymeric body includes a first aqueous-swellable, biocompatible and biodegradable polymer having a thickness. The aqueous-swellable and biodegradable polymer retaining structural integrity for up to thirty days when swollen and kept moist by a moist aqueous environment. The geometric or non-geometric shape of the polymeric body may be optimized to fit the surrounding anatomy and may take any one of a variety of shapes including but not limited to cylinders, rectangles, triangles, cones, star shapes, rhomboids, and/or random undefined shapes. Similarly, the lumen may be in shapes including but not limited to cylinders, rectangles, triangles, cones, star shapes, rhomboids, and/or random undefined shapes. Barrier layers of biodegradable polymer may be used to prevent migration of liquids into the lumen; said layers may have the additional features of being elastic and/or aqueous-swellable, being capable to lend structural support to the stent, and having variable and tunable degradation rates.

BRIEF DESCRIPTION OF THE FIGURES

FIG. 1A is a perspective of a device (which may be used as an ostial stent) that includes a compressed foam structure and a collapsed lumen that is not visible to the naked eye.
FIG. 1B is a perspective of a device that also includes a compressed foam structure with a clearly visible lumen.
FIG. 1C is a perspective of a swollen foam cylindrical tube with a central lumen.
FIG. 2A is a perspective of a variant of the device shown in FIG. 1C, that includes a swollen foam, a lumen, and a barrier layer.
FIG. 2B a perspective similar to the device in FIG. 2A, but with differently located barrier layer.
FIG. 3A is a perspective of a compressed foam stent with a plurality of lumens, where the said lumens are completely collapsed.
FIG. 3B is a perspective of a compressed foam with a plurality of lumens that are collapsed or at least partially open and further expand or remain open upon expansion of the compressed foam via addition of a liquid.
FIG. 3C is a perspective of an altered device that includes a swollen foam with a plurality of lumens that pass all the way through the device and a lumen that terminates to produce a blind hole in the device.
FIG. 4A shows a side view of the location of a non-swollen device comprised of a compressed foam with a central lumen inside a narrowing in the human body and not in contact with the surrounding anatomy.
FIG. 4B shows a side view of a device that includes both a foam that has been swollen via the addition of a fluid and a central lumen.

DETAILED DESCRIPTION OF THE INVENTION

Figure 1:
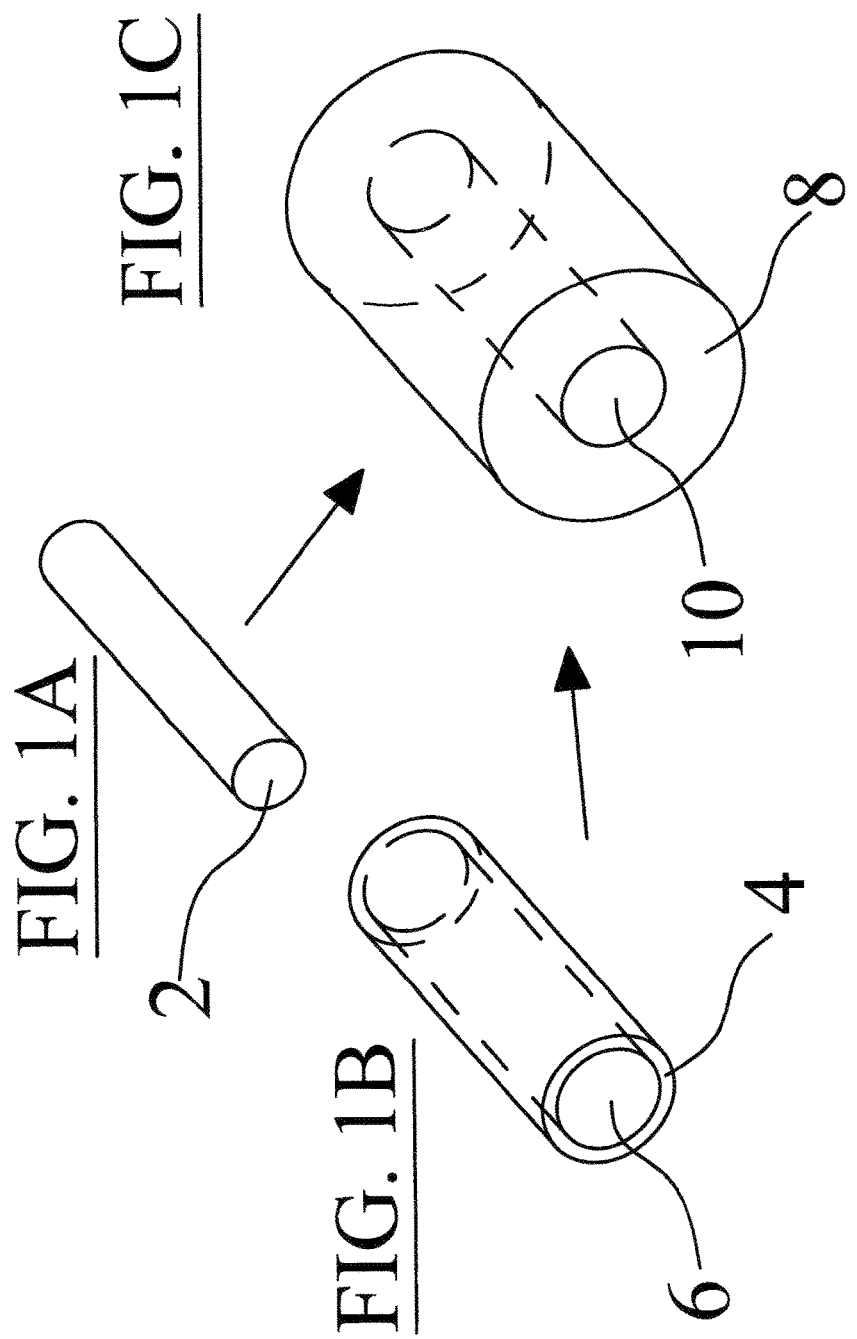
FIG. 1 includes FIGS. 1A, 1B and 1C.

A polymeric stent according to the present inventive technology shall be described heretofore as a cylindrical polymeric tube with a cylindrical lumen, with the understanding that a multitude of other shapes are possible as previously described. The polymeric tube may have a length, an outer surface and a cross-section, with a lumen passing through the entire length. The lumen has an outer surface forming a diameter that is an internal diameter of the cylindrical polymeric tube. The polymeric tube is constructed from a first aqueous-swellable, biocompatible and biodegradable polymer or mixture of polymers having a thickness. The aqueous-swellable and biodegradable stent should retain structural integrity for up to thirty days when swollen and kept moist by a moist aqueous environment. By structural integrity it is meant that the cylindrical polymeric tube remains capable of supporting the lumen in an open condition, allowing fluid flow there through for the designated time period (three days, five days, 7 days, ten days, etc,). By being biodegradable it is meant that the composition of the tube structure deteriorates into absorbable, dissolvable, dispersible or decomposable size materials so that the tube materials do not persist in the body to any harmful degree. Aqueous soluble or dispersible materials are good examples of materials that break down into small, body dispersible particles sizes, such as less than millimeter diameters, and even to micron-size and/or sub-micron diameters.

The stent may have the internal diameter surface composed of a second biodegradable polymeric composition layer that is less aqueous-swellable than the first aqueous-swellable and biodegradable polymer(s) and the second biodegradable polymeric composition layer having a thickness that is less than 50% the thickness of the first biodegradable polymeric composition layer. The 50% dimension is fairly high in proportions, as the second layer need be only a film structure acting as a barrier layer. The second biodegradable composition layer may afford the stent addition mechanical integrity and may serve to control the rate of liquid and or solute transport into the lumen. The second biodegradable polymeric composition may be of the same chemical nature as the first biodegradable composition (e.g., polyester, acrylic, polysaccharide, starch, and hydrolyzable polymers that break down into biologically harmless chemical units or dissolve under normal conditions in the human body), in which case the second layer may be less swellable due to a relative increase in density, polymer/polymer interactions, or chemical bonds between polymers. Alternatively, the second biodegradable composition may be of a different chemical nature than the first biodegradable composition.

The stent may further have an outer surface composed of a third biodegradable polymeric composition layer that is less aqueous-swellable than the first aqueous-swellable and biodegradable polymer and the third biodegradable polymeric composition layer having a thickness that is less than 50% the thickness of the first biodegradable polymeric composition layer. The thickness of the third layer is to assist in prevent passage of excess liquid into the lumen or into the body of the cylindrical tube and then into the lumen. The 50% dimension is fairly high in proportions, as the third layer need be only a film structure acting as a barrier layer. The third layer should also be decomposable/degradable, as it would otherwise remain in the ostia where the tubes have been placed. Even though the third layer is of smaller dimensions, it is seldom desirable to leave unnatural materials within human cavities such as the ostia. Some prior art systems have required physical (surgical) removal of the stents, which can often lead to tearing of the tissue that had been previously supported and even protected by the stent. To that end, prior art materials often had to be constructed with critically smooth surfaces to prevent damage on removal and avoid growth of tissue bonding to uneven sites on the prior art stents. As the present stents decompose, their surface characteristics can be less critical.

In alternate embodiments, a barrier layer may be located internally within the splint, such that it is at some location between the internal and external surfaces of the device. In all locations, the barrier layer may constitute a dense polymer layer, or the barrier layer may possess an intrinsic porosity. The barrier layer(s) may or may not be continuous along the corresponding surface of the stent. One or more barrier layers may impart additional structural integrity to the stent in dry and/or wet states for all or a portion of the residence time of the stent in the body. A given barrier layer may degrade at the same or at a different rate than one or more other barrier layers or than the body of the polymeric stent.

The stent may have the first aqueous-swellable and biodegradable polymer degradable by immersion in human mucous for a period of up to 30 days.

Depending on specific medical intent, this period may be shorter or longer, and can be controlled by appropriate selection of compositions used.

The stent may be composed wherein the first, second, third or other aqueous-swellable and biodegradable polymers are selected from the group consisting of hydrolysable polymers, aqueous-dispersible, fragmentable and aqueous-soluble polymers, such as cellulosic polymers, polyesters, polysaccharides, starches, sugars, chitosan and chitosan derivatives (these former materials may be partially cross-linked to adjust their desired physical properties) and other materials known in the medical field to be bioabsorbable, as with stitches and other temporary implants.

A method of maintaining an open ostium comprising inserting into the ostium a polymeric stent can include steps in which:

a cylindrical polymeric tube having a length, an outer surface, a cross-section, with a lumen passing through the entire length, the lumen having a surface forming a diameter that is an internal diameter of the cylindrical polymeric tube is provided;

the polymeric tube includes a first aqueous-swellable, biocompatible and biodegradable polymer having a thickness;

the aqueous-swellable and biodegradable polymer retaining structural integrity for at least one hour (for purposes of allowing clotting and protecting a wound), at least six hours, at least one day, at least five days, or even at least up to thirty days (for longer short-term benefits) when swollen and kept moist by a moist aqueous environment, the method further including:

allowing natural fluids within the ostium to swell the first aqueous-swellable, biocompatible and biodegradable polymer or introducing artificial aqueous solution to swell the aqueous-swellable, biocompatible and biodegradable polymer;

wherein the swelling expanding the cylindrical polymeric tube against tissue within the ostium to secure the cylindrical polymeric tube within the ostium.

The method may allow the cylindrical tube to remain in the ostium and allow natural body fluids to degrade the first biodegradable polymeric composition layer such that integrity of the cylindrical tube is reduced.

The method may further include using a structure wherein the internal diameter surface is composed of a second biodegradable polymeric composition layer that is less aqueous-swellable than the first aqueous-swellable and biodegradable polymer and the second biodegradable polymeric composition layer has a thickness that is less than 50% the thickness of the first biodegradable polymeric composition layer, and allowing the cylindrical tube to remain in the ostium also allows natural body fluids to degrade the second biodegradable polymeric composition layer and degrade integrity of the cylindrical tube is further reduced.

The method may function wherein expanding the cylindrical polymeric tube against tissue within the ostium allows distal ends of the polymeric tube to expand to diameters greater than a middle section of the cylindrical polymeric tube. This provides a bow-tie appearance to the inserted and swollen stent.

A further understanding of the practice of the invention will be appreciated by a review of the Figures.

FIG. 1: FIG. 1A depicts a device (which may be used as an ostial stent) that includes a compressed foam structure (2) and a collapsed lumen that is not visible to the naked eye. FIG. 1B depicts a device that also includes a compressed foam structure (4), but is different from the device in FIG. 1A, as it also includes a clearly visible lumen (6) that passes all the way down the long axis of the device. The devices depicted in FIGS. 1A and 1B expand via the addition of liquid to produce an altered device (depicted in FIG. 1C) that includes a swollen foam (8) with a central lumen (10).

Figure 2:
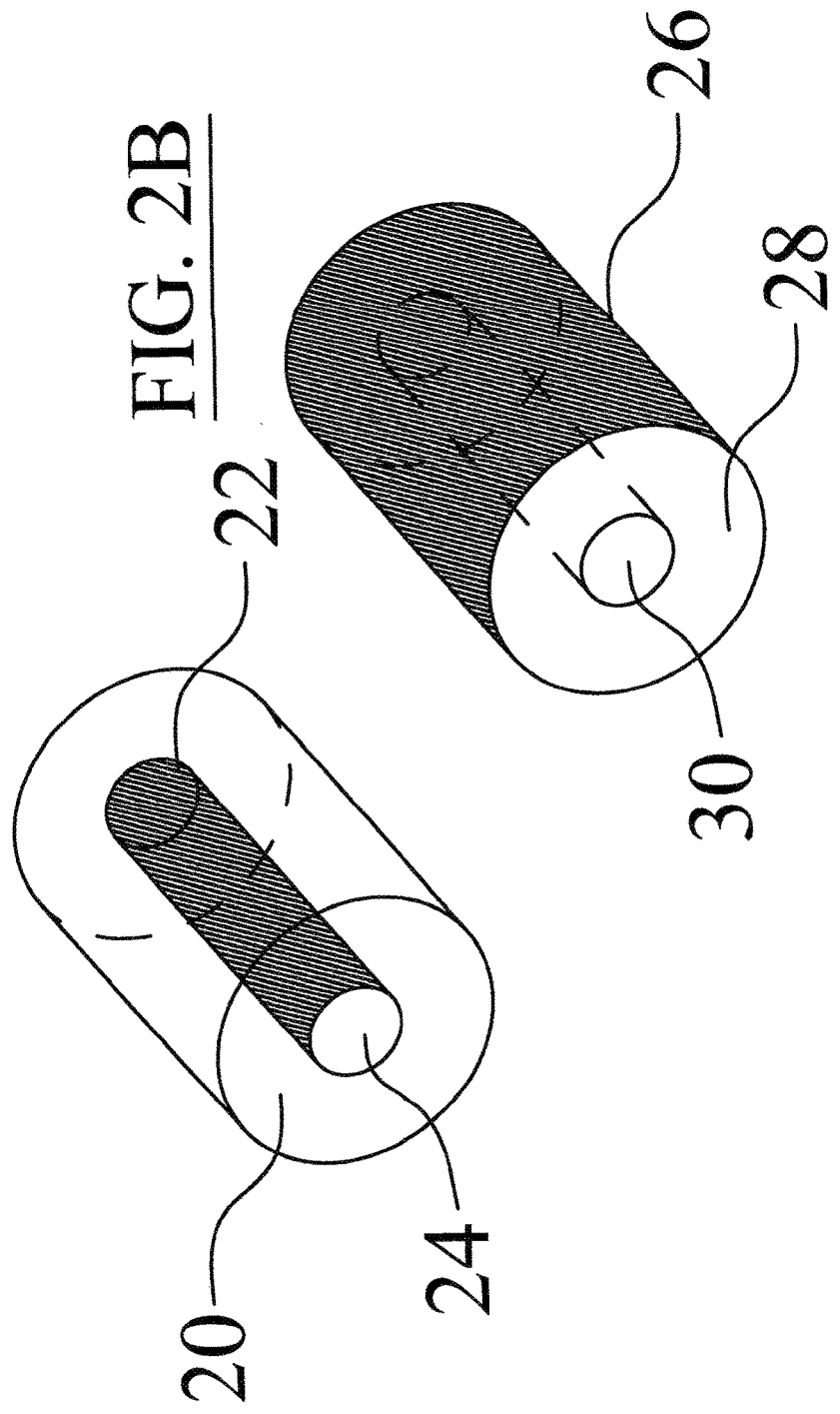
FIG. 2 includes FIGS. 2A and 2B.

FIG. 2: FIG. 2A depicts a variant of the device shown in FIG. 1C, that includes a swollen foam (20) that has expanded via the addition of a liquid, a lumen (24), and a barrier layer (22) designed to control the transport of solvents and solutes along the lumen wall. The device illustrated in FIG. 2B is similar to the device in FIG. 2A, and it has a swollen foam (28) that has expanded via the addition of a liquid and a lumen (30); however, the device in FIG. 2B is different from the device in FIG. 2A, as it has a barrier layer (26) designed to control the transport of solvents and solutes on the outer surface of the device rather than on the lumen.

Figure 3:
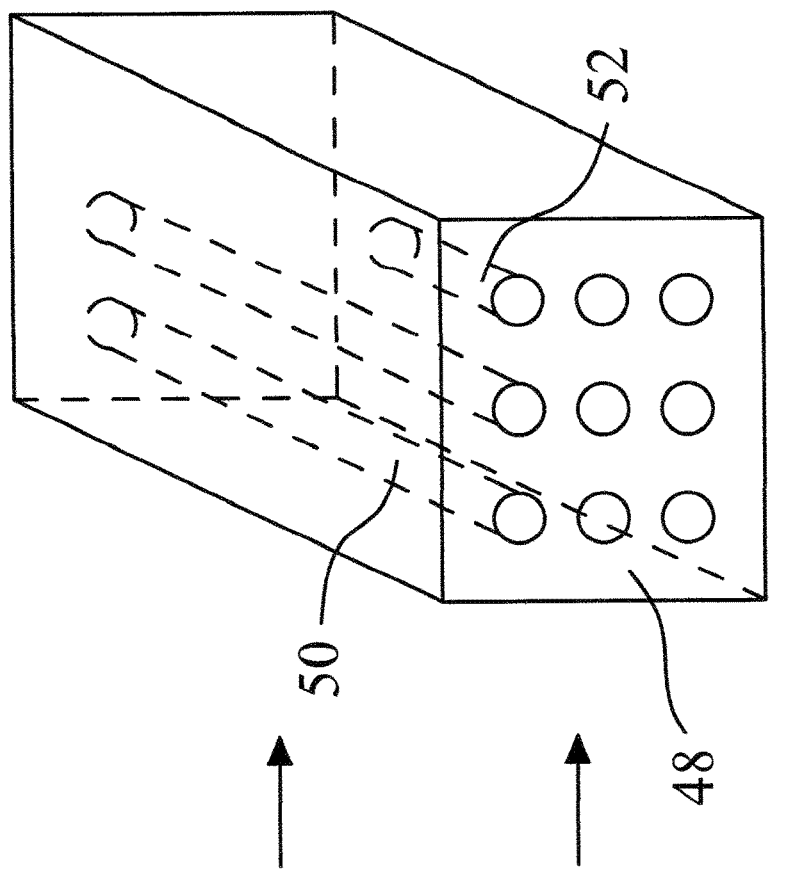
FIG. 3 includes FIGS. 3A and 3B.

FIG. 3: The device in FIG. 3A includes a compressed foam (40) with a plurality of lumens, where the said lumens are completely collapsed. The device in FIG. 3B includes a compressed foam (42) with a plurality of lumens that are collapsed or at least partially open and further expand or remain open upon expansion of the compressed foam via addition of a liquid. One of the depicted lumens passes all the way through the device in FIG. 3B (44) and one of the depicted lumens terminates part way through the device to produce a blind hole (46). The devices illustrated in FIGS. 3A and 3B expand via the addition of liquid to produce an altered device (depicted in FIG. 3C) that includes a swollen foam (48) with a plurality of lumens that pass all the way through the device (50) and a lumen that terminates to produce a blind hole (52) in the device. The blind hole can be used by the medical practitioner as a delivery port for injecting liquid into the swellable polymeric cylindrical core to preferentially deliver the liquid to the stent and prevent loss of the liquid out of the distal end.

Figure 4:
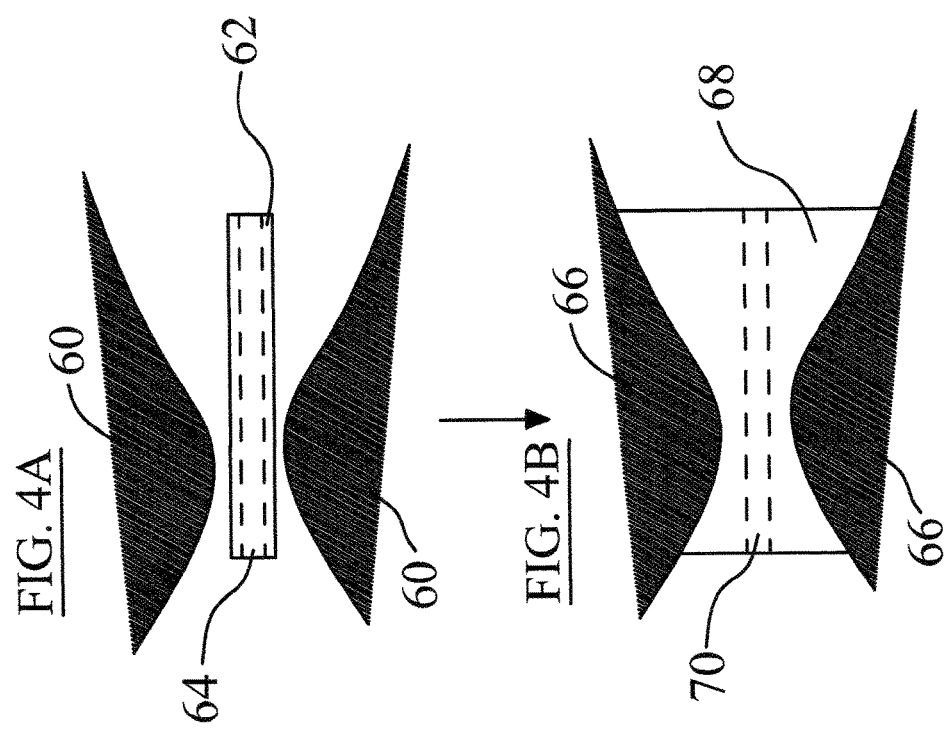
FIG. 4 includes FIGS. 4A and 4B.

FIG. 4: FIG. 4A shows the location of a device comprised of a compressed foam (62) with a central lumen (64) inside a narrowing in the human body and not in contact with the surrounding anatomy (60). FIG. 4B shows a device that includes both a foam (68) that has been swollen via the addition of a fluid and a central lumen (70). The swollen foam has expanded to make contact with and conform to the shape of the surrounding anatomy (66) via expansion of the originally compressed device depicted in FIG. 4A.

Other aspects of the technology can be practiced within the practice of the invention as described. Newer synthetic or polymeric materials meeting the described properties can be used. The geometric shape of the polymeric body may be optimized to fit the surrounding anatomy and may take any one of a variety of shapes including but not limited to cylinders, rectangles, triangles, cones, star shapes, rhomboids, and/or random undefined shapes. Similarly, the lumen may be in shapes including but not limited to cylinders, rectangles, triangles, cones, star shapes, rhomboids, and/or random undefined shapes. Longitudinal reinforcement of the various shapes may be used (with biodegradable materials). The dimensions and ratios of the dimensions may be varied. For example, in the case of a cylinder, the ratio of the inside diameter of the lumen to the length of the device on the unswelled device can vary between 1:2 and 1:30, preferably between 1:3 and 1:20. Similarly, the ratio of the inside diameter of the lumen to the outside diameter may vary between 1:1.1 to 1:10 in an unswelled state and from 1:1.5 to 1:20 in a swollen state. Other variations are within the ordinary skill of the designer.

The devices are intended to provide a persistent open lumen through the ostium, and minimize any damage that might occur during removal.

Where the outmost surface (and even the innermost surface) is a barrier layer, it may also be somewhat elastic to allow the polymer to swell. The cylinder shape of the device may also be conical, and the cross-sections (of the body and the lumens) can be any geometric of irregular shape.

What is claimed:

1. A method of maintaining an open nasal ostium comprising inserting into the ostium of a nasal pasage a polymeric stent comprising:
   a cylindrical polymeric tube having a length, an outer surface, a cross-section, with a lumen passing through the entire length, the lumen having a surface forming a diameter that is an internal diameter of the cylindrical polymeric tube;
   the cylindrical polymeric tube comprising a first aqueous-swellable, biocompatible and biodegradable polymer having a thickness;
   the aqueous-swellable and biodegradable polymer retaining structural integrity for at least one hour when swollen and kept moist by a moist aqueous environment in a nasal passage in the ostium, the method further comprising:
   allowing natural fluids within the nasal ostium to swell the first aqueous-swellable, biocompatible and biodegradable polymer or introducing artificial aqueous solution into the nasal passage to swell the aqueous-swellable, biocompatible and biodegradable polymer;
   wherein the swelling expands the cylindrical polymeric tube against tissue within the nasal ostium to secure the cylindrical polymeric tube within the nasal ostium.

2. The method of claim 1 wherein the cylindrical tube is allowed to remain in the nasal ostium and natural body fluids degrade the first biodegradable polymeric composition layer and degradation sufficient to collapse the cylindrical tube occurs within 1 to thirty days in the natural body fluids while in contact with the tissue.

3. The method of claim 2 wherein the internal diameter surface comprises a second biodegradable polymeric composition layer that is less aqueous-swellable than the first aqueous-swellable and biodegradable polymer and the second biodegradable polymeric composition layer having a that is less than 50% the thickness of the first biodegradable polymeric composition layer, and allowing the cylindrical tube to remain in the nasal ostium also allows natural body fluids to degrade the second biodegradable polymeric composition layer.

4. The method of claim 1 wherein expanding the cylindrical polymeric tube against tissue within the nasal ostium allows distal ends of the polymeric tube to expand to diameters greater than a middle section of the cylindrical polymeric tube.

5. The method of claim 1 wherein the cylindrical polymeric tube, in addition to the lumen, also has at least one blind hole entering the cylindrical polymeric tube from one end and not exiting the cylindrical polymeric tube from another end, and wherein an aqueous fluid is directed within the nasal passage in the ostium and into the at least one blind hole to increase a rate of swelling for the cylindrical polymeric tube after it has been positioned within an ostium.

6. The method of claim 2 wherein the cylindrical polymeric tube, in addition to the lumen, also has at least one blind hole entering the cylindrical polymeric tube from one end and not exiting the cylindrical polymeric tube from another end, and wherein an aqueous fluid is directed into the nasal passage in the ostium and into at least one blind hole to increase a rate of swelling for the cylindrical polymeric tube after it has been positioned within the nasal ostium.

7. The method of claim 3 wherein the cylindrical polymeric tube, in addition to the lumen, also has at least one blind hole entering the cylindrical polymeric tube from one end and not exiting the cylindrical polymeric tube from another end, and wherein an aqueous fluid is directed into the nasal passage of the ostium and into at least one blind hole to increase a rate of swelling for the cylindrical polymeric tube after it has been positioned within the nasal ostium.

8. The method of claim 1 wherein the lumen initially expands its diameter when natural body fluids in the nasal passage of the ostium or an artificial aqueous solution introduced into the nasal passage in the nasal ostium swell the first aqueous-swellable, biocompatible and biodegradable polymer.

9. The method of claim 6 wherein the lumen initially expands its diameter when natural body fluids within the nasal passage of the nasal ostium or an artificial aqueous solution put into the nasal passage of the nasal ostium swell the first aqueous-swellable, biocompatible and biodegradable polymer.

10. A method of maintaining an open nasal ostium comprising inserting into a nasal passage of the nasal ostium a polymeric stent comprising:
a cylindrical polymeric tube having a length, an outer surface, a cross-section, with a lumen passing through the entire length, the lumen having a surface forming a diameter that is an internal diameter of the cylindrical polymeric tube;
the cylindrical polymeric tube comprising a first aqueous-swellable, biocompatible and biodegradable polymer having a thickness;
the aqueous-swellable and biodegradable polymer retaining structural integrity for at least one hour when swollen within the nasal passage of the nasal ostium and kept moist by a moist aqueous environment within the nasal passage of the nasal ostium, the method further comprising:
allowing natural fluids within the nasal ostium to swell the first aqueous-swellable, biocompatible and biodegradable polymer or introducing artificial aqueous solution into the nasal passage of the nasal ostium to swell the aqueous-swellable, biocompatible and biodegradable polymer.

* * * * *